United States Patent [19]
Leonard et al.

[11] 3,993,461
[45] Nov. 23, 1976

[54] CARDIOTOMY RESERVOIR

[75] Inventors: Ronald J. Leonard, Harvard; Jonathan Wayne Takagishi, Arlington Heights, both of Ill.

[73] Assignee: Baxter Laboratories, Inc., Deerfield, Ill.

[22] Filed: Dec. 9, 1974

[21] Appl. No.: 531,018

Related U.S. Application Data

[63] Continuation-in-part of Ser. No. 381,311, July 20, 1973, Pat. No. 3,891,416.

[52] U.S. Cl. ............................. 55/178; 210/436; 210/DIG. 23
[51] Int. Cl.² ........................................ B01D 19/02
[58] Field of Search ............. 55/178; 210/433, 436, 210/438, 440, 443, 497 R, DIG. 23

[56] References Cited
UNITED STATES PATENTS

| | | | |
|---|---|---|---|
| 3,237,770 | 3/1966 | Humbert, Jr. | 210/438 |
| 3,384,242 | 5/1968 | Kudlaty | 210/436 |
| 3,507,395 | 4/1970 | Bentley | 210/443 |
| 3,701,433 | 10/1972 | Krakauer et al. | 210/436 |
| 3,768,653 | 10/1973 | Brumfield | 210/436 X |
| 3,891,416 | 6/1975 | Leonard et al. | 210/436 X |

*Primary Examiner*—Charles N. Hart
*Assistant Examiner*—Richard W. Burks
*Attorney, Agent, or Firm*—Louis Altman; Garrettson Ellis

[57] ABSTRACT

A reservoir for the collection, purification, and storage of blood during surgical procedures which comprises a hollow blood storage casing having a hollow, perforated member within said casing extending from end-to-end thereof. Blood defoaming means and a filter are carried by the hollow member, so that the blood defoamer and filter are noncollapsible, and extend the entire length of the chamber within the casing, with one of the ports communicating with the interior of the hollow member, so that blood passes through the perforations of the hollow member and defoamer-filter means.

8 Claims, 5 Drawing Figures

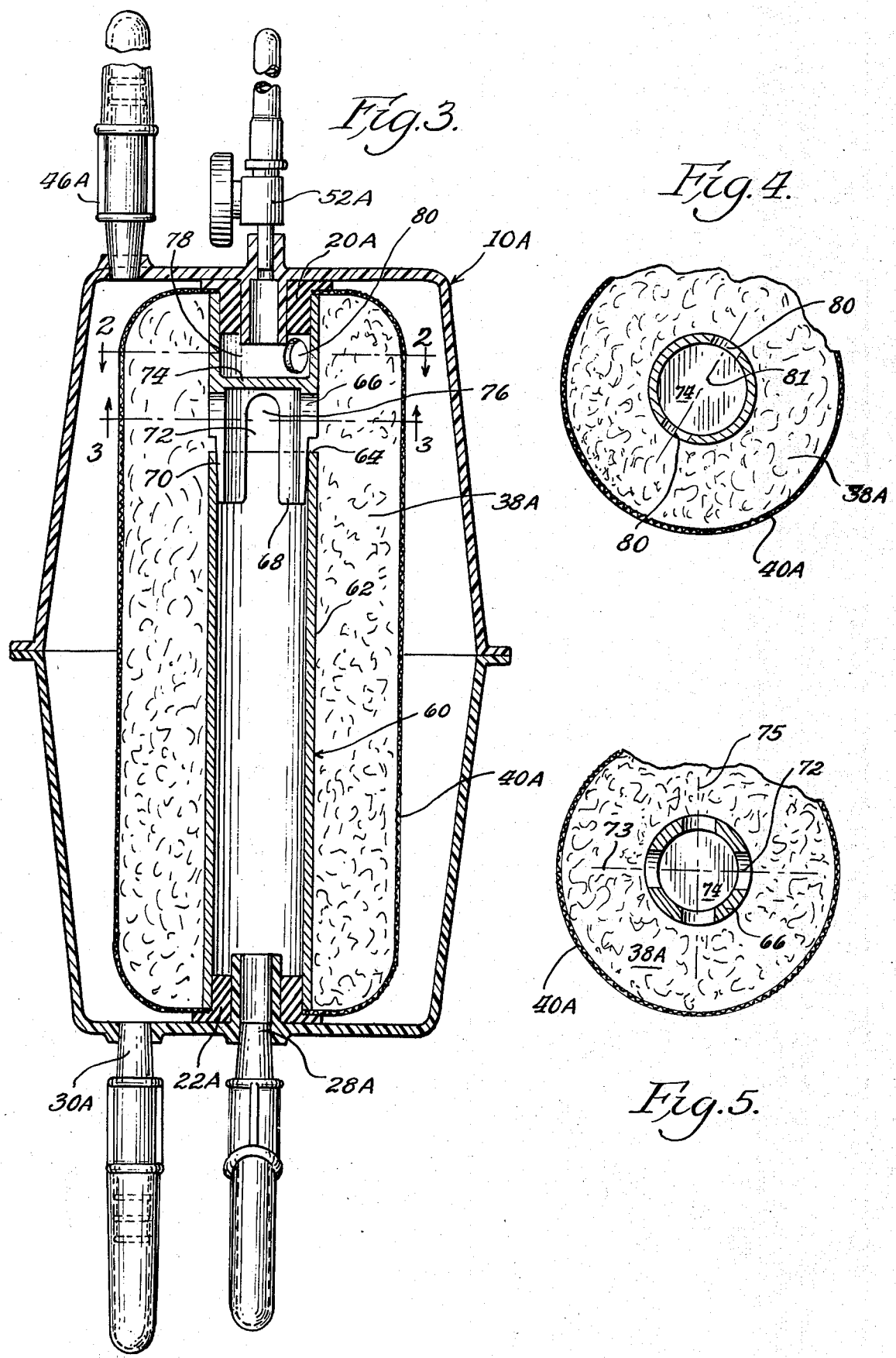

CARDIOTOMY RESERVOIR

CROSS REFERENCE TO RELATED APPLICATION

This application is a continuation-in-part of co-pending Application Ser. No. 381,311, filed July 20, 1973 and now patent No. 3,891,416.

BACKGROUND OF THE INVENTION

Cardiotomy reservoirs are used during major surgery to collect blood which has been accumulated in a surgical incision site or elsewhere by an air-driven cardiotomy sucker or the like.

It is very desirable to reinfuse this blood into the patient since a patient's own blood is far superior to any donated blood that he can receive. However, blood which has been removed from an incision site is likely to contain small clots and other forms of solid debris, which should not be reinfused into the patient.

Hence, blood is passed into the cardiotomy reservoir, where it passes through a filter to remove air bubbles and the undesirable solid debris, and where it can be stored under blood preserving conditions until the surgeon elects to return the blood to the patient, which is usually immediately after purification of the blood.

The prior art device of U.S. Pat. No. 3,507,395 is commercially available and widely used as a cardiotomy reservoir. However, it has certain disadvantages which limit its effective use. First, the filter of the prior art reservoir is unsupported, and thus is subject to collapse under certain conditions of use. Also, the filter does not extend the entire length of the unit. Hence, air from cardiotomy suckers entering along with the blood into the reservoir must migrate through the filter, and may bubble through filtered blood prior to reaching the vent from which the air leaves the reservoir. This may initiate the formation of small bubbles in the filtered blood, and have other bad effects.

Similarly, any resupply of blood which is added to the prior art cardiotomy reservoirs in the conventional manner at the upper end thereof is not filtered prior to infusion to the patient. Hence, the small clots which may be present in resupply blood (which may come fresh from a blood bag or the like) are not removed prior to infusion.

DESCRIPTION OF THE INVENTION

In accordance with this invention, the above problems of prior art cardiotomy are eliminated, and a cardiotomy reservoir which is easy to manufacture and which can provide improved utilization of the filter material is provided.

The invention of this application comprises a reservoir for the collection, purification, and storage of blood during surgical problems, including a hollow blood storage casing having a first port positioned at one end thereof and a hollow member positioned within the casing and extending from end-to-end thereof. The hollow member is generally a tube having a bore positioned to communicate at one end with the first port. The wall of the hollow member defines perforations for the flow of blood through the wall between the interior and the exterior of the hollow member. Also, the hollow member carries a filter for the defoaming and other purification of blood.

A second port is positioned adjacent the same end of the casing as the first port, exterior of the hollow member, so that a blood flow path is defined between the first port, the hollow member and filter means, and the second port.

The hollow member is generally rigid, providing internal support for the casing, to prevent the ends of it from doming inwardly when the reservoir is placed under reduced pressure. Also, the hollow member serves as a support member for the filter, so that the filter will not collapse under unfavorable conditions, as in the prior art devices.

A blood resupply port is positioned at the end of the casing opposite the blood inlet and outlet, to communicate with the interior of the filter member, so that resupplied blood must pass through the filter before administration to the patient. A vent port also typically communicates with the upper end of the bore of the tubular member, so that gas entering at the bottom of the hollow member will not enter into contact with filtered blood, but will pass through the length of the hollow member out of the vent port.

As a further advantage, the bore of the hollow member is typically about 2 or 3 times the diameter of the first port, which is typically the inlet port. Hence, the volume of blood contained by the bore of the hollow member is relatively low compared with the corresponding volume of blood within the filter member of U.S. Pat. No. 3,507,395. Thus, in the device of this invention, the level of unprocessed blood tends to rise higher in the bore than a similar volume of unprocessed blood in the prior art reservoir, the result of which is to permit the blood to enter into contact with a larger amount of the available defoaming and filter material, which results in more efficient defoaming and filtering.

In the drawings,

FIG. 3 is an elevational view of another embankment of the cardiotomy reservoir of this invention shown in partial vertical section.

FIG. 4 is a fragmentary sectional view taken along line 2—2 of FIG. 3.

FIG. 5 is a fragmentary sectional view taken along line 3—3 of FIG. 3.

Figure 1:
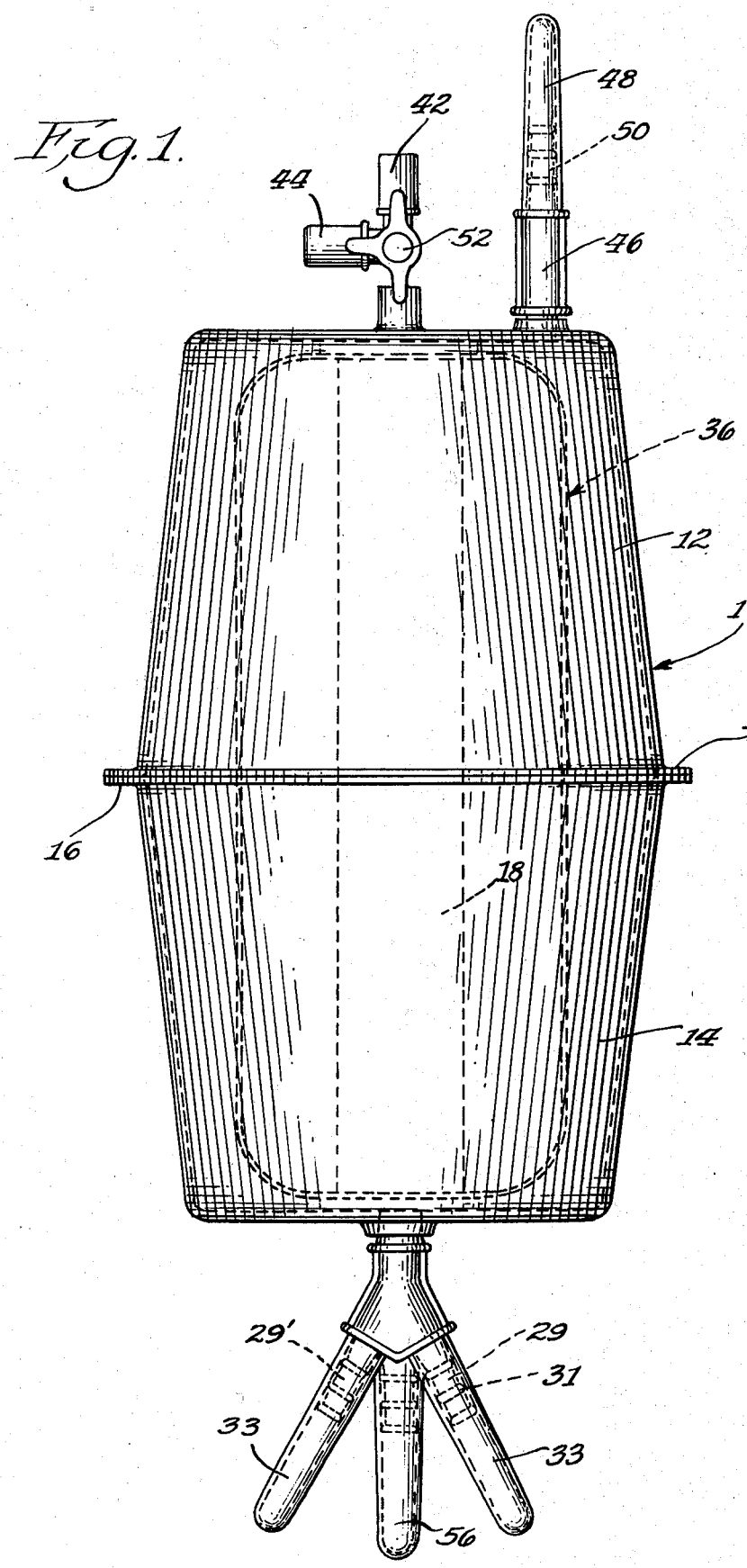
FIG. 1 is an elevational view of a typical cardiotomy reservoir of this invention.
Figure 2:
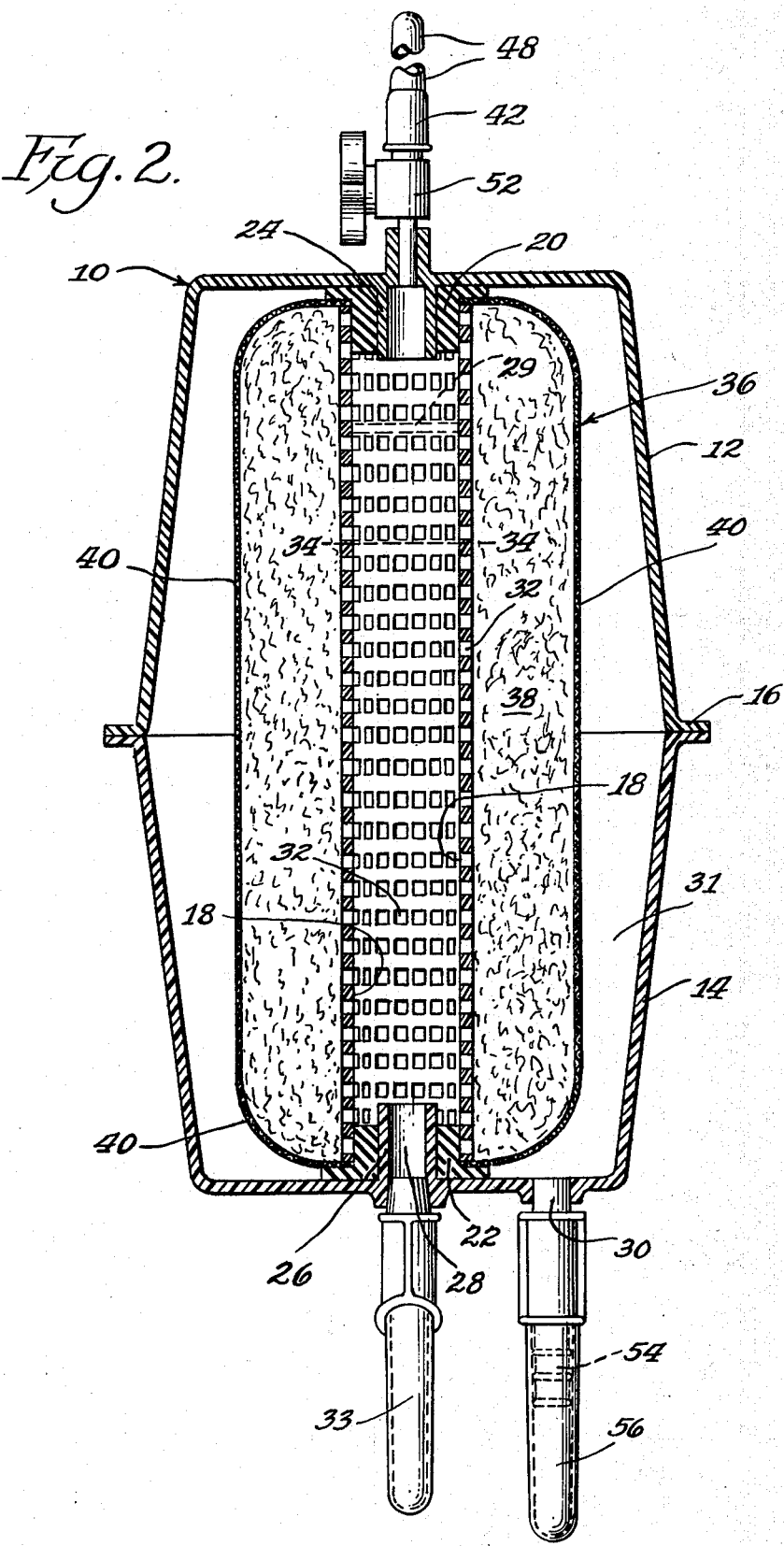
FIG. 2 is an elevational view of the cardiotomy reservoir of FIG. 1, rotated 90° about its longitudinal axis and shown in partial vertical section.

Referring to FIGS. 1 and 2, the cardiotomy reservoir of this invention has a casing 10, which comprises a pair of mating shells 12, 14, which are sealed together along their respective flanges 16 by an appropriate method such as heat sealing or solvent sealing, to provide an enclosed, blood-receiving chamber.

Hollow member 18 is typically a tube made of perforated polyethylene or another suitable plastic material, and extends from end-to-end of casing 10, being sealed at the ends by elastomeric plugs 20, 22, for leak-proof sealing. Plugs 20, 22, in turn, are secured in position about tubular sections 24, 26, which are typically integrally molded parts of casing halves 12 and 14 respectively. Tubular extension 26 serves to define first port 28, which communicates with one end of the bore of tubular member 18 and typically serves as the blood inlet to the reservoir. Second port 30 is defined in a conventional manner with a plastic tubular insert at the same end of casing 10 as first port 28, but in a position exterior to the hollow, tubular member 18. As a result of this, the blood flow path through the reservoir enters by way of first port 28, passing through the perforations of tubular member 18 to chamber 31 exterior of the tubular member, and then out by way of second port 30.

Perforations 32 of tubular member 18 are of a size to provide uniform, low resistance flow of blood through the wall of the tubular member. Perforations 32 can be, for example, about ⅛ inch square, or larger, fewer, round holes about ¼ inch in diameter can be used, or any other suitable dimension.

The perforations 32 can be distributed along the entire length of hollow member 18. Alternatively, a portion of the tubular member nearest first port 28 can be free of perforations, for about ½ to ¾ of the length of hollow member 18, for example up to about line 34—34, to force the blood entering the bore of hollow member 18 to rise in the bore and thus spill out into a central or upper portion of the filter means 36 carried by hollow member 18. Thus, the blood is introduced to the filter means 36 at an intermediate place along its length, and can spill downwardly through the filter means, enlarging the area of the filter means used even at low flow rates of blood. Also, this prevents filtered blood from returning to the bore of hollow member 18.

First port 28 can communicate with branched connectors 29, 29' having conventional barbs 31 to facilitate connection to elastomeric tubing. This permits blood from more than one source to be provided to the reservoir.

Connectors 29, 29' are sealed with conventional removable sheaths 33 to maintain sterility prior to use.

Filter means 36 is shown to comprise two components: a blood defoaming means 38, which may conventionally be made of spun metal or plastic fibers carrying an organosilicon defoaming agent, surrounded and retained by a tubular filter 40, which can be made of nylon fabric mesh having openings in the range of 20 to 200 microns, preferably about 120 microns in width, to permit blood cells and other natural components of blood to pass through the fabric 40, but to prevent the passage of blood clots and other solid debris.

The fibers of the defoaming means 38 and tubular filter 40 are carried about tubular member 18. The ends of tubular filter 40 are secured by pinching between the respective ends of tubular member 18 and sealing members 20, 22, so that the ends of the tubular filter 40 are tightly retained between the ends of the tubular member and the casing to prevent collapse of filter 40 and the defoaming means 38 contained therein.

Barrier 29 is shown in dotted lines to indicate that it can optionally be present to occlude the bore of hollow member 18. This prevents the mixing of blood entering first port 28 and blood entering resupply port 44 (FIG. 1) prior to filtering, when it is desired to prevent such mixing.

At the upper end of the reservoir, a vent port 52 is provided for the removal of air or other gas which enters the reservoir along with the blood through first port 28. When barrier 29 is not used, gas entering the reservoir can pass directly upwardly through the bore of tubular member 18 and out of vent port 52 without coming into contact with filtered blood, which can reside in chamber 31 exterior to filter 40. Another vent port 46 (FIG. 1) can be provided for the additional venting of gas which is collected in the area exterior to filter member 36. Port 46 is shown with a conventional sterile sealing member 48 which can be removed prior to use, and barbs 50 on the port for reliable sealing connection with an elastomeric tube, if desired. Vent port 46 can also be connected to a vacuum line to provide suction filtration of the blood when desired.

Also, the function of ports 42 and 46 can be interchanged, or one of these ports can also be used for monitoring pressure during operation.

Upper tubular member 24 is in communication with a conventional three-way valve 52 which controls access through a branched conduit leading alternatively to vent port 42 and a blood resupply port 44, which are shown to be closed with conventional removable sealing sleeves. Blood resupply port 44 can be connected to an extra source of blood such as a unit of donated blood in a blood bag. The administration of this donated blood to the patient by way of the reservoir of this invention can be controlled by appropriate manipualtion of valve 52. When extra blood is not being administered through port 44, valve 52 can be manipulated to close port 44 and open vent port 42 for normal operation. Any donated blood which is administered is delivered to the bore of hollow member 18, so that it must pass through filter member 36 prior to administration to the patient by way of the second port 30, which is typically the outlet port. Valve 52 also has a completely closed position for use during suction or the like. Outlet port 30 also includes a barbed nozzle 54 to facilitate the sealed connection with an elastomeric tube, and a sterile sealing sleeve 56 of conventional design, which is removed prior to use.

Referring to FIG. 3, a modified embodiment of the cardiotomy reservoir of this invention is shown, which is basically similar in structure to the cardiotomy reservoir of FIG. 1, except for the differences as shown and described herein.

Casing 10A is similar in structure to the previous embodiment, as is first port 28A and its related parts, and second port 30A which typically functions as an outlet port in the manner of the previous embodiment. Valve 52A functions as a fluid resupply port in a manner similar to the previous embodiment, but does not need a branched port as in the previous embodiments since it typically does not vent. Vent port 46A can be provided to function in a manner similar to vent port 46 of FIG. 1. Plugs 20A, 22A are similar in construction to plugs 20 and 22 of the previous embodiment.

The hollow member 60 of this embodiment, corresponding to member 18 of the embodiment of FIGS. 1 and 2, is considerably different. Hollow member 60 comprises a tubular member 62 which is free of perforations, and is carried at one end adjacent to inlet 28A by plug 22A. Tube 62 is shorter than the length of casing 10A, and is retained at its end 64 by adaptor member 66, which fits at one end about plug 20A for sealing retention and projects at its other end 68 into the bore of tubular member 62. Adaptor member 66 defines several tapered surfaces 70 for sliding rention within the bore of tubular member 62. Adaptor member 66 defines several open ports or perforations 72 to permit blood passing through inlet 28A to spill from the interior of hollow member 60 into defoaming means 38A and tubular filter 40A, which may be similar to members 38 and 40 of the embodiment of FIGS. 1 and 2, and may be attached about hollow member 60 in similar manner. Accordingly, essentially all of the filtering and defoaming means 38A, 40A can be utilized by forcing the blood to rise in tubular member 62 to near the top of casing 10A before being permitted to spill outwardly into filter and defoaming means 38A, 40A respectively. From there, the blood spills downwardly and outwardly through defoaming means 38A and filter 40A, from where it can be withdrawn through outlet 30A.

Adaptor 66 also defines a partition 74 to define a pair of chambers, 76, 78. Chamber 76 is open to the interior of tubular member 62 and communicates with the exterior through ports 72. The other chamber 78 communicates with priming and blood resupply port 52A. Chamber 78 also defines a pair of second ports 80 which are diametrically opposed to each other (only one of which is shown in FIG. 3 due to the vertical sectional representation of adaptor 66). The diametric axis 81 between ports 80 is horizontally skewed with respect to a diametric axes 73, 75 between ports 72, so that fluid passing out of ports 80 will not pass in large amounts into ports 72.

The advantage of the above permits the priming of the reservoir of this invention with blood or parenteral solution by its addition through supply port 52A. The blood or other priming solution then passes out of apertures 80, for the most part into the region exterior of hollow member 60. The priming solution is generally desired to be placed into casing 10A in a position exterior of hollow member 60, while avoiding the placing of large quantities of priming solution into hollow member 60 itself.

The embodiment of FIG. 3 is advantageous in that it eliminates the need for expensive tubing having large numbers of perforations, as in the embodiment of FIGS. 1 and 2, and replaces such structure with a less expensive solid, tubular member 62, and an easily moldable adaptor member 66, which two parts together define a hollow member 60, providing the internal re-enforcement for casing 10A, and defining ports or large perforations 72 for communication of blood between the interior and exterior of hollow member 60.

In accordance with this invention, an improved cardiotomy reservoir is provided having a number of substantial advantages over the prior art cardiotomy reservoirs. The device is internally reinforced to resist heavy suction pressure when such is necessary, and a filter member is provided in which more of the area is more uniformly utilized, rather than a large portion of the area being overutilized and the remainder underutilized. Furthermore, air and other gases entering the reservoir can be vented without contacting the freshly filtered blood, and the filter member can be reliably secured in position, without danger of collapse, and without sewing or other laborious processes, by a simple clamping operation.

The above has been offered for illustrative purposes only, and is not to be considered as limiting the invention, which is defined in the claims below.

That which is claimed is:

1. A reservoir for the collection, purification, and storage of blood during surgical procedures which comprises: a hollow blood storage casing having a first port positioned at one end thereof; a hollow member positioned within said casing and extending from end-to-end thereof, said hollow member having a bore positioned to communicate at one end thereof with said first port, said hollow member comprising (1) a tubular member having a wall free of perforations, said one end of the hollow member which is positioned to communicate with the first port being defined by an end of said tubular member, and (2) an adaptor member in engaged relation with the other end of said tubular member, and defining first port means for communication between the interior and exterior of said hollow member, said adaptor member being affixed to said casing end which is remote from the end of said casing which carries said first port, to firmly position said hollow member relative to said casing, said hollow member also carrying about its exterior filter and defoaming means for the purification of blood, a second port communicating through the casing in a position exterior to said hollow member, whereby a blood flow path is defined through said first port, hollow member, first port means, filter means, and second port; and a third port carried by said remote casing end and positioned in communication with said adaptor member.

2. The reservoir of claim 1 in which said adaptor member defines a pair of chambers, and a partition separating said chambers, one of said chambers being open to the interior of said tubular member and defining said first port means for communication between the interior and exterior of said hollow member, the other of said chambers communicating with said third port, said adaptor member defining second port means for communication between the interior of said other chamber of the adaptor and the exterior of said hollow member.

3. The reservoir of claim 2 in which said filter means is positioned along essentially the entire length of said hollow member.

4. The reservoir of claim 3 in which said second port means occupy a different circumferential position on said adaptor member than said first port means, whereby fluid passing out of said second port means will not pass in large amounts into said first port means.

5. The reservoir of claim 4 having an additional vent port exterior to said hollow member and positioned at an end opposite said first port.

6. The reservoir of claim 5, in which said tubular member extends for a major portion of the length of said hollow member.

7. The reservoir of claim 3 in which said filter is flexible and tubular, and is secured about said hollow member by securance of the ends of said tubular filter between the ends of said hollow member and the casing.

8. The reservoir of claim 7 in which the bore of said tubular member is about 2 to 3 times greater in cross sectional dimension than the cross sectional dimension of said first port.

* * * * *

UNITED STATES PATENT AND TRADEMARK OFFICE
CERTIFICATE OF CORRECTION

PATENT NO. : 3,993,461
DATED : November 23, 1976
INVENTOR(S) : Ronald J. Leonard et al.

It is certified that error appears in the above-identified patent and that said Letters Patent are hereby corrected as shown below:

Column 1, line 55, delete "problems" and substitute therefor --procedures--.

Column 4, line 16, delete "manipualtion" and substitute therefor --manipulation--.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*